（12）United States Patent
Welker

(10) Patent No.: US 6,818,045 B2
(45) Date of Patent: Nov. 16, 2004

(54) LIQUID SEPARATOR WITH INTEGRAL SIGHT GLASS

(75) Inventor: Brian H. Welker, Sugar Land, TX (US)

(73) Assignee: Welker Engineering Company, Sugar Land, TX (US)

( * ) Notice: Subject to any disclaimer, the term of this patent is extended or adjusted under 35 U.S.C. 154(b) by 56 days.

(21) Appl. No.: 10/289,187

(22) Filed: Nov. 5, 2002

(65) Prior Publication Data

US 2004/0083891 A1 May 6, 2004

(51) Int. Cl.[7] .......................... B01D 53/22; B01D 35/30
(52) U.S. Cl. .................. 96/11; 96/4; 96/416; 55/385.1; 55/429; 55/432; 55/433; 55/487; 55/523; 73/863.23; 73/864.51
(58) Field of Search ..................... 96/4, 11, 12, 416; 55/385.1, 395, 429, 432, 433, 486, 487, 490, 523, 525, DIG. 17; 73/863.23, 864.51

(56) References Cited

U.S. PATENT DOCUMENTS

| | | | | | |
|---|---|---|---|---|---|
| 2,526,782 | A | * | 10/1950 | Thorpe | 96/416 |
| 4,323,375 | A | * | 4/1982 | Chang | 96/416 |
| 4,544,387 | A | * | 10/1985 | Agerlid | 96/416 |
| 4,572,725 | A | * | 2/1986 | Kojima | 96/416 |
| 4,707,168 | A | * | 11/1987 | Mizutani | 96/416 |
| 5,442,968 | A | * | 8/1995 | Westlake et al. | 73/863.23 |
| 5,800,597 | A | * | 9/1998 | Perrotta et al. | 96/11 |
| 6,284,026 | B1 | * | 9/2001 | Lai | 96/416 |
| 6,357,304 | B1 | * | 3/2002 | Mayeaux | 73/863.23 |
| 6,672,135 | B2 | * | 1/2004 | Adiletta | 73/863.23 |

OTHER PUBLICATIONS

*Welker Sampling Accessories*; Welker Engineering Company Product Distribution Catalog; 2001; Sugar Land, Texas, US.
*WelkerFilters, Filter Dryers Dumps and Accessories*; Welker Engineering Company Product Distribution Catalog; 2001; Sugar Land, Texas, US.
*Obtaining Natural Gas Samples for Analysis by Gas Chromatography*; Gas Processors Association; 2000; pp. 1–14; GPA Standard 2166–86; Tulsa, OK, US.

\* cited by examiner

*Primary Examiner*—Duane Smith
*Assistant Examiner*—Jason M. Greene
(74) *Attorney, Agent, or Firm*—Blackwell Sanders Peper Martin LLP

(57) ABSTRACT

The liquid separator with integral sight glass separates liquids, if present, from gases and allows a technician to visually confirm the presence or absence of liquids in the gas. The present invention is typically used when taking a spot sample from a natural gas pipeline. Spot samples of natural gas are often analyzed by gas chromatographs which do not tolerate the presence of liquids in a sample. If the technician visually confirms the presence of liquids, adjustments to the spot sampling technique can be made to possibly eliminate the creation of such liquids due to poor technique.

30 Claims, 2 Drawing Sheets

LIQUID SEPARATOR WITH INTEGRAL SIGHT GLASS

BACKGROUND OF INVENTION

1. Field of the Invention

Gases, such a natural gas, are often analyzed by gas chromatographs. Other chromatographs are used to analyze liquids. Some gases may have entrained liquids that cannot be analyzed by gas chromatographs. One use of the present invention is to separate liquids from gases so the gas can be analyzed by a gas chromatograph.

2. Description of Prior Art

Spot sampling is a procedure that is well known in the natural gas industry and is commonly used. For example, the Gas Processors Association ("GPA") has established standard 2166 for proper spot sampling techniques. Spot samples of natural gas are taken in the field from a pipeline and placed in a sample cylinder. The sample cylinder and the gas sample are then transferred from the field to a laboratory for analysis, frequently by a gas chromatograph. Because gas chromatographs cannot analyze liquids, it is desirable to try and keep liquids out of spot samples or in the alternative, alert the laboratory when unavoidable liquids are encountered so appropriate measures can be taken to safeguard the chromatograph.

Welker Engineering Company of Sugar Land, Tex., the assignee of the present patent application, has previously sold a sight glass without a filter called the model SG3. The SG3 sight glass was primarily used with odorant injection systems to provide visual confirmation that the odorant was being properly injected into the system. The SG3 was also used to provide visual confirmation in other chemical injection systems that used glycol. In some situations, the SG3 has been used at a spot sampling station to visually determine if liquid was being transferred into a sample cylinder. The SG3 did not prevent liquids from entering a sample cylinder.

Welker Engineering Company has also previously sold a filter without a sight glass called the LE2. The LE2 filter has been used at spot sampling stations to keep liquids out of sample cylinders. However, the LE2 did not provide any visual information to the personnel that were taking the spot sample.

Other companies, such as A+ Corporation of Prairieville, Louisiana also sell liquid separators and filters to keep liquids out of sample cylinders at spot sampling stations. Some of these products from A+ are described in the company web site (www.apluscorporation.com). Pages from this web site are included in the Information Disclosure Statement filed concurrently herewith. In summary, the prior art filters and liquid separators from both Welker Engineering Company and A+ Corporation do not incorporate a sight glass. There is a need to incorporate a sight glass with a liquid separator so operators may modify their technique while a spot sample is being taken. Some liquids can be eliminated through the modification of spot sampling techniques; other naturally occurring liquids many be unavoidable and will persist even if the spot sampling techniques are modified.

When a spot sample is being taken, improper technique can lead to the unwanted creation of liquids due to the Joule-Thomson effect. Running natural gas through valves and/or a sample cylinder during a spot sampling operation can create a sharp pressure drop which may chill the gas and lead to condensation of unwanted liquids. If an operator can visually observe that liquids are present, adjustments may be made to the sampling technique that will reduce or eliminate the creation of unwanted liquids. A more representative spot sample will be taken if condensation does not occur during the sampling operation which can lead to creation of unwanted liquids.

However, even if proper techniques are used, some natural gases have entrained liquids that cannot be eliminated by adjusting spot sampling techniques. In these circumstances, it is necessary to have a liquid separator to keep the sample dry for the gas chromatograph. There is a need for a liquid separator that incorporates a sight glass to enhance spot sampling operations.

SUMMARY OF INVENTION

The present invention is a combination sight glass and liquid separator. The present apparatus may be used at spot sampling stations to adjust technique and eliminate liquids from the sample. The present invention includes a high pressure glass window that allows the apparatus to operate at pressures up to 2,000 psi. An optional protective shield protects the glass window from inadvertent damage. A membrane filter is porous to gas and substantially impermeable to liquids. A polytetrafluoroethylene membrane is positioned on a porous sintered stainless steel support. Other membranes and supports may also be suitable provided they allow the gas to pass and stop the liquids. A drain is positioned in the liquid separator to drain liquids from the apparatus.

DETAILED DESCRIPTION

Figure 1:
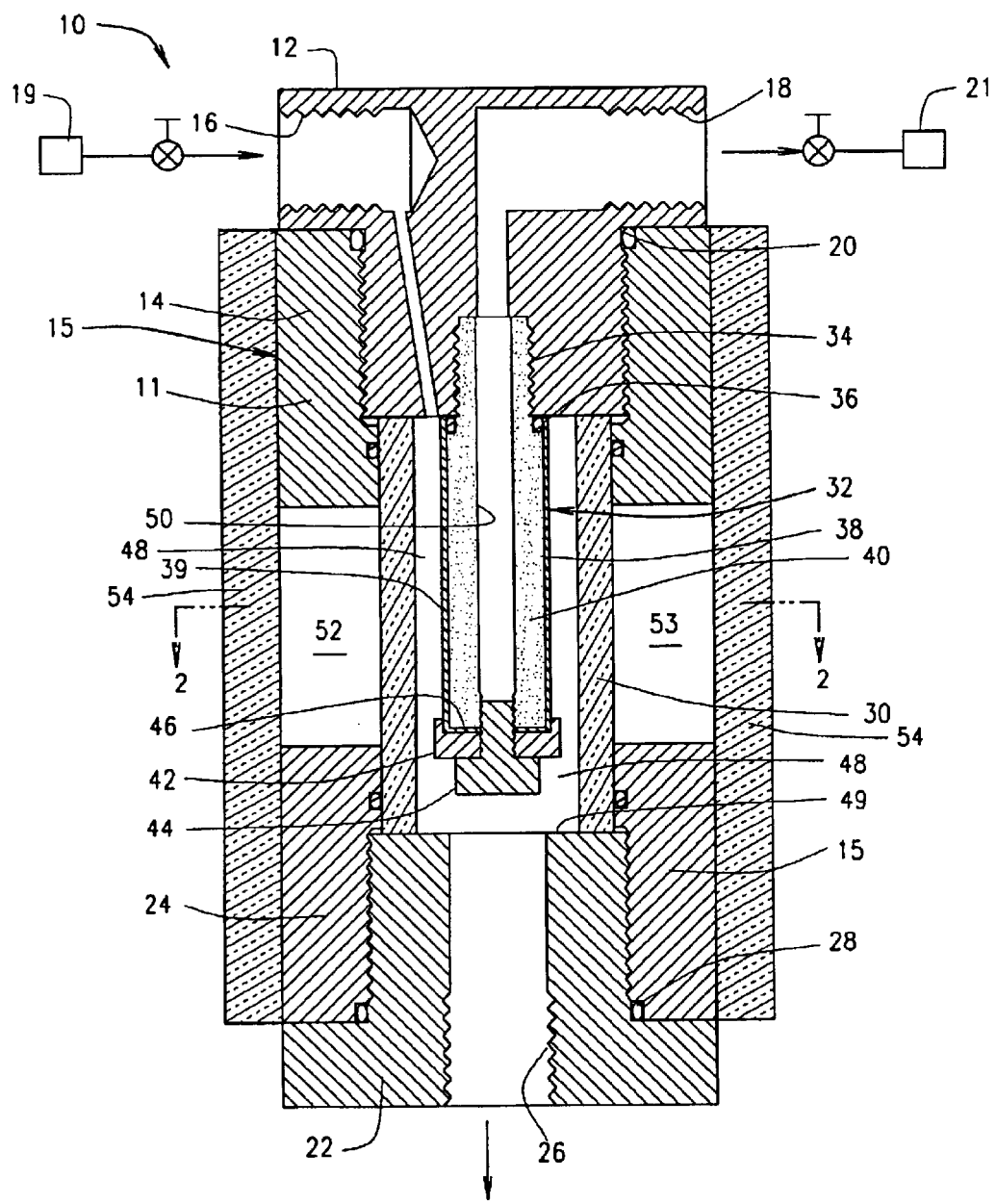
FIG. 1 is a cross-section view of the liquid separator with integral sight glass.

FIG. 1 is a cross-section view of the liquid separator with integral sight glass which is generally identified by the numeral 10. The separator 10 includes a body 15 comprising a body portion 11. with an inlet cat, 14 and drain cap 22 secured thereto. The inlet cap 12 threadably engages the upper section 14 of the body portion 11. The inlet cap 12 defines an inlet 16 and an outlet 18. The inlet 16 is connected to a source 19 of gas and the outlet 18 allows connection of a sampling container 20 to the seiarator 10. An o-ring 20 seals the inlet cap 12 to the body portion 11 of body 15. In the preferred embodiment, the o-ring is formed from Viton® a brand of fluoroelastomers produced by Du Pont de Nemours, E. I. & Company of Wilmington, Del. Other elastomeric seals may also be suitable for use in this invention. A drain cap 22 threadably engages the lower portion 24 of the body portion 11 of body 15. The drain cap 22 defines a drain 26. A drain valve, not shown, is connected to the drain 26 and is normally in the closed position. When fluid accumulates in the liquid separator 10, the drain valve, not shown, may be opened to drain the fluid. An o-ring 28 seals the drain cap 22 to the body portion 11 of body 15. In the preferred embodiment, the o-ring 28 is also formed from Viton brand fluoroelastomers; however, other elastomers may also be suitable for use in this invention. A glass cylinder 30 is mounted in the body portion ii and is captured between the inlet cap 12 and the drain cap 22 in the body 15. In the preferred embodiment, the glass is Gold Dot brand tempered glass from Corning of Coming, N.Y. Other brands of glass may be suitable for use in this invention provided they are capable of withstanding the operating pressure of the fluids that pass through the apparatus 10.

A filter assembly 32 threadably engages the inlet cap 12 at filter assembly port 34. An o-ring 36 seals the filter assembly 32 to the inlet cap 12. In the preferred embodiment, the o-ring 36 is also formed from Viton brand fluoroelastomers; however, other elastomers may also be suitable for use in this invention.

The filter assembly includes a membrane 38 positioned on a support 40. The membrane is permeable to gases and impermeable to liquids. In the preferred embodiment, the membrane is formed from Teflon® brand tetrafluoroethylene fluorocarbon polymer produced by Du Pont de Nemours, E. I. Company. However, other membranes may be suitable in this invention provided that they achieve separation of gas from liquids. For example, Tyvek® brand material from Du Pont de Nemours, E. I. Company may also be suitable as well as Millipore four micron filter paper from Pall Specialty Materials, Charlotte, N.C. Nylon and/or cat gut may also be suitable. The only requirement for the membrane is that it be gas permeable and impermeable to liquids.

In the preferred embodiment, the porous support 40 is formed from sintered stainless steel. However, other supports are within the scope of this invention provided that they allow gas to pass to the outlet 18 and support the membrane 38.

An end cup 42 contains the membrane 38 against the support 40. A bolt 44 threadably engages the free end 46 of the support 40 and holds the end cup 42 and the membrane 38 against the support 40. A chamber 48 is defined by the inside surface of the glass cylinder 30, the inlet cap 12 and the drain cap 22. The filter assembly 32 is positioned in the chamber 48. The filter assembly has a hollow bore 50 that allows gas to flow from the chamber 48, through the filter assembly 32 to the outlet 18.

The body portion 11 of body 15 defines opposing windows 52 and 53 that allow a technician positioned outside the liquid separator 10 to look into the chamber 48 to determine the presence of liquids, if any. In some situations, the technician can see the formation of liquids on the outside surface 39 of the membrane 38. In other situations, the liquid will pool in the bottom 49 of the chamber 48 and will rise to a level that can be seen through the windows 52 and 53. Liquids are undesirable when samples are to be analyzed by gas chromatographs. To protect the glass cylinder 30 from inadvertent damage, a transparent plastic shield 54 is mounted on the exterior of the body 15 and is positioned to cover the windows 52 and 53. In the preferred embodiment, the plastic shield is formed from Plexiglas® brand thermoplastic poly(methylmethacrylate)-type polymers sold by Robin and Haas Company of Philadelphia, Pa. However, other polymers that are transparent and shatter resistant may also be suitable in this invention.

Figure 2:
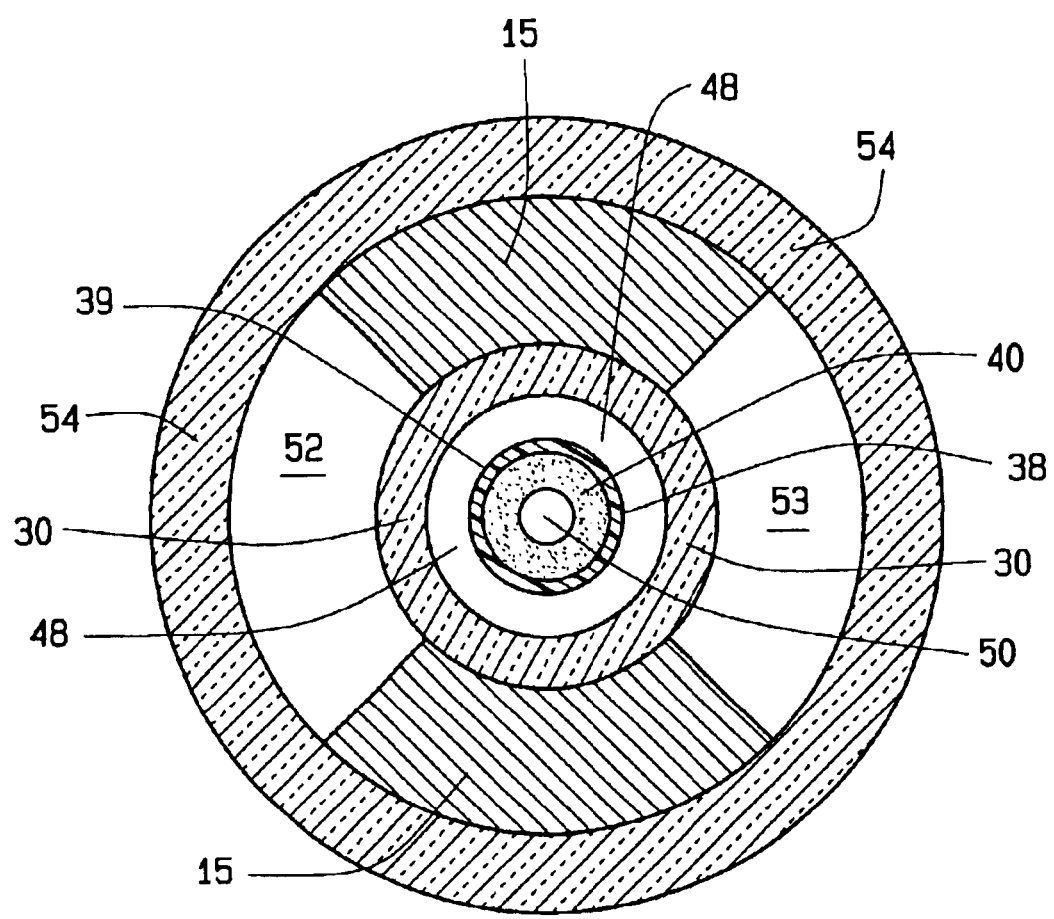
FIG. 2 is a cross-section view of the liquid separator with integral sight glass along the line 2—2 of FIG. 1.

FIG. 2 is a section view of the liquid separator with integral sight glass 10 taken along the line 2—2 of FIG. 1. The protective shield 54 is positioned on the outside of the body 15 to provide protection to the glass cylinder 30. Windows 52 and 53 are formed in the body 15 to allow a technician positioned outside the liquid separator 10 to look through the transparent shield 54 and the transparent cylinder 30 and see inside the chamber 48. The primary purpose of being able to look inside the chamber 48 is to detect the presence of liquids so that the sampling technique may be modified to possibly eliminate the creation of liquids. Some naturally occurring liquids may not be eliminated by modification of sampling technique, so the separator is an integral part of this invention to consistently produce dry samples for analysis by a gas chromatograph.

Operation of the Preferred Embodiment

Pipeline gas enters the liquid separator with integral sight glass through the inlet 16 and passes through the inlet cap 12 to the chamber 48. The drain 26 is connected to a valve that is normally in the closed position. The pipeline gas may have liquids therein. As the gas passes through the filter assembly 32, any unwanted liquids accumulate on the outside of the filter assembly and eventually fall by gravity to the bottom of the chamber and to the drain 26. A technician positioned outside the apparatus can look through the window 52 and see the presence of liquids on the outside of the filter assembly. This gives the technician the opportunity to adjust the spot sampling technique to possibly eliminate the liquids. The gas passes through the filter assembly 32 and the bore 50 into the outlet 18 which is connected to a sample container, not shown. From time to time, it may be necessary to open the drain valve, not shown, to discharge accumulated liquids from the apparatus.

A spot sampling station is positioned proximate a natural gas pipeline, typically in a remote location. The spot sampling station includes a manifold connected to a probe in the pipeline by tubing and valves. These valves are typically in the off position. A pipeline technician will travel to the spot sampling station to take a spot sample. This merely provides a snapshot of the gas traveling through the pipeline on the given day and moment when the sample is taken.

The technician brings a sample container to the spot sampling station. An empty sample cylinder is commonly used for this purpose. The empty sample cylinder typically has an inlet valve on one end and an outlet valve on the other end. The empty sample cylinder is connected to the manifold and both valves on the cylinder are opened. Valves on the manifold are then opened to blow gas through the empty sample cylinder.

After the sample cylinder has been purged, the outlet valve on the sample cylinder is closed which raises the pressure in the sample cylinder to pipeline pressure. The inlet valve on the sample cylinder is then closed, isolating the sample cylinder from the pipeline. The outlet valve on the sample cylinder is then opened, thus exhausting the pressurized natural gas in the sample cylinder to atmosphere. This procedure is then repeated several times. During this fill and discharge process, the technician should look into the liquid separator to see if liquids are present in the chamber.

If liquids are present in the chamber, modifications can be made to the sampling technique, to possibly eliminate creation of the liquids. These modifications are well known to those skilled in the art and involve adjustments to the outlet valve on the sample cylinder and perhaps elsewhere on the spot sampling station. Unfortunately, not all liquids can be eliminated so the liquid separator is an integral part of this invention to assure dry samples. After the sample has been taken, the sample cylinder is taken to a laboratory for analysis by gas chromatographs and perhaps other instruments.

What is claimed is:

1. A liquid separator apparatus is in fluid communication with a source of natural gas and a removable sample container, the separator comprising:

a body at least partially defining a chamber, an inlet in fluid communication with the source of natural gas, an outlet in fluid communication with the removable sample container, and a drain to permit removal of entrained liquids from the chamber, a first transparent window structure mounted in the body to allow an individual positioned outside the liquid separator to view an interior of the chamber;

a second transparent member mounted to the body and positioned exterior of the first transparent window structure to shield said first transparent window structure;

a filter assembly positioned in the chamber and connected to the outlet, the filter assembly separating entrained liquids from the natural gas whereby substantially dry gas passes from the liquid separator to the removable sample container; and the filter assembly having;

a membrane that is permeable to gas and substantially impermeable to liquids and a porous support for the membrane.

2. The apparatus of claim 1 wherein the second transparent member includes a transparent plastic shield to protect the first transparent window structure from inadvertent damage.

3. The apparatus of claim 2 wherein the membrane is formed from polytetrafluoroethylene.

4. The apparatus of claim 1 wherein the drain is in fluid communication with a valve, which is normally in a closed position, but when opened allows discharge of the separated liquid from the chamber.

5. A liquid separator comprising:

a body at least partially defining a chamber and including a body portion, an inlet in fluid communication between the chamber and a source of pressurized gas, an outlet in fluid communication with the chamber, and a drain to remove liquids from the chamber;

a first transparent window structure positioned in the body portion to allow an individual positioned outside the liquid separator to view an interior of the chamber;

a second transparent member mounted to the body and positioned exterior of the first transparent window structure; and a filter assembly in fluid communication with the chamber and the outlet, the filter assembly having a membrane that is substantially permeable to gases and substantially impermeable to liquids whereby liquid is separated from the gas as the gas passes through the filter assembly to the outlet.

6. The apparatus of claim 5 wherein the second transparent member including a transparent plastic shield to protect the first transparent window structure from inadvertent damage.

7. The apparatus of claim 6 wherein the membrane is formed from polytetrafluoroethylene.

8. The apparatus of claim 7 wherein the first transparent window structure is formed from glass rated to withstand up to 2000 psi of pressure.

9. The apparatus of claim 8 wherein the second transparent member is formed from thermoplastic poly(methyl methacrylate)-type polymers.

10. The apparatus of claim 5 further including a support for the membrane, the support formed from sintered stainless steel.

11. A liquid separator comprising:

a body having an inlet cap and a drain cap with a transparent cylinder captured between the caps, the transparent cylinder and the caps further defining an interior chamber that can be viewed through the transparent cylinder by an individual located on an outside of the liquid separator;

the interior chamber in fluid communication with a source of gas the gas having entrained liquids and the interior chamber in fluid communication with a drain;

a filter assembly in fluid communication with the interior chamber and the outlet, the filter assembly having a membrane that separates entrained liquids from the gas as the gas passes through the filter assembly to the outlet; and a transparent shield to protect the transparent cylinder from inadvertent damage.

12. The apparatus of claim 11 wherein the membrane is formed from polytetrafluoroethylene.

13. The apparatus of claim 12 wherein the transparent cylinder is formed from glass rated to withstand up to 2000 psi of pressure.

14. The apparatus of claim 13 wherein the transparent shield is formed from thermoplastic poly(methyl methacrylate)-type polymers.

15. The apparatus of claim 11 further including a support for the membrane, the support formed from sintered stainless steel.

16. The apparatus of claim 1 wherein the first transparent window structure including a generally cylindrical transparent member having opposite open ends and an interior bore with at least a portion of the filter assembly being positioned within a portion of the interior bore.

17. The apparatus of claim 16 wherein the first transparent window structure is formed from glass rated to withstand up to 2000 psi of pressure.

18. The apparatus of claim 17 wherein the second transparent member is formed from thermoplastic poly(methyl methacrylate)-type polymers.

19. The apparatus of claim 18 wherein the support is formed from sintered stainless steel.

20. The apparatus of claim 16 wherein the first transparent window structure including a window formed in the body and positioned between an outer surface of the generally cylindrical transparent member and an interior surface of the second transparent member.

21. The apparatus of claim 5 wherein the first transparent window structure including a generally cylindrical transparent member having opposite open ends and an interior bore with at least a portion of the filter assembly being positioned within a portion of the interior bore.

22. The apparatus of claim 21 wherein the first transparent window structure including a window formed in the body and positioned between an outer surface of the generally cylindrical transparent member and an interior surface of the second transparent member.

23. The apparatus of claim 11 wherein the first transparent window structure including a generally cylindrical transparent member having opposite open ends and an interior bore with at least a portion of the filter assembly being positioned within a portion of the interior bore.

24. The apparatus of claim 23 wherein the first transparent window structure including a window formed in the body and positioned between an outer surface of the generally cylindrical transparent member and an interior surface of the second transparent member.

25. A liquid separator is in fluid communication with a source of natural gas and a removable sample container, the separator comprising:

a chamber having an inlet in fluid communication with the source of natural gas, an outlet in fluid communication with a removable container, and drain to permit removal of entrained liquids from the chamber and transparent window to allow an individual positioned outside of the liquid separator to view an interior of the chamber, said transparent window being formed from glass rated to withstand up to 2,000 psi of pressure;

a transparent plastic shield to protect the transparent window from inadvertent damage;

a filter assembly positioned in the chamber and connected to the outlet, the filter assembly separating entrained liquids from the natural gas whereby substantially dry gas passes from the liquid separator to the removable sample container; and the filter assembly having:
    a membrane formed from polytetrafluoroethylene that is permeable to gas and substantially impermeable to liquid; and
    a porous metal support for the membrane.

26. The apparatus of claim 25 wherein the transparent shield is formed from thermoplastic poly(methyl methacrylate)-type polymers.

27. The apparatus of claim 26 wherein the support is formed from sintered stainless steel.

28. A liquid separator comprising:
a body defining a chamber, the chamber having an inlet in fluid communication with a source of pressurized gas, an outlet, and a drain to remove liquids from the chamber;

a transparent window positioned in the body to allow an individual positioned outside the liquid separator to view an interior of the chamber, and transparent window being formed from glass rated to withstand up to 2,000 psi of pressure;

a transparent plastic shield to protect the transparent window from inadvertent damage; and a filter assembly in fluid communication with the chamber and the outlet, the filter assembly having a membrane formed from polytetrafluoroethylene that is substantially permeable to gas and substantially impermeable to liquid whereby liquid is separated from the gas and the gas passes through the filter assembly to the outlet.

29. The apparatus of claim 28 wherein the transparent window is formed from glass rated to withstand up to 2000 psi of pressure.

30. The apparatus of claim 29 further including a support for the membrane, the support formed from sintered stainless steel.

* * * * *

UNITED STATES PATENT AND TRADEMARK OFFICE
CERTIFICATE OF CORRECTION

PATENT NO. : 6,818,045 B2
DATED : November 16, 2004
INVENTOR(S) : Brian H. Welker It is certified that error appears in the above-identified patent and that said Letters Patent is hereby corrected as shown below:

Column 2,
Line 43, delete "cat" and replace with -- cap --;
Line 48, delete "seiarator" and replace with -- separator --;
Line 64, delete "body portion ii" and replace with -- body portion 11 --;
Line 67, delete "Coming, N.Y." and replace with -- Corning, N.Y." --;

Column 3,
Line 54, delete "Robin" and replace with -- Rohm --; and

Column 5,
Line 7, delete "transnarent" and replace with -- transparent --.

Signed and Sealed this

Fifteenth Day of February, 2005

JON W. DUDAS
*Director of the United States Patent and Trademark Office*